United States Patent [19]

Matsuura et al.

[11] 4,202,828
[45] May 13, 1980

[54] PROCESS FOR SEPARATION OF NAPHTHOQUINONE AND PHTHALIC ACID

[75] Inventors: Ryo Matsuura, Yamato; Tatsuyoshi Komatsu, Kamakura; Yukio Nomiyama, Yokohama; Kenji Usui, Nihonbashi, all of Japan

[73] Assignee: Kawasaki Kasei Chemicals Limited, Tokyo, Japan

[21] Appl. No.: 868,349

[22] Filed: Jan. 10, 1978

[51] Int. Cl.$^2$ .................. C07C 45/24; C07C 49/66; C07C 51/48; C07C 63/16

[52] U.S. Cl. .................. 260/396 R; 562/408; 562/485; 562/486; 562/487

[58] Field of Search .................. 260/396 R; 562/485, 562/486, 408, 487

[56] References Cited

U.S. PATENT DOCUMENTS

| | | | |
|---|---|---|---|
| 2,536,833 | 1/1951 | Bailey | 260/396 R |
| 2,783,251 | 2/1957 | Sayward | 260/396 R |
| 3,379,741 | 4/1968 | Tschamper et al. | 260/396 R |

FOREIGN PATENT DOCUMENTS

| | | | |
|---|---|---|---|
| 242124 | 8/1965 | Austria | 260/396 R |
| 1239286 | 4/1967 | Fed. Rep. of Germany | 260/396 R |
| 49-132042 | 12/1974 | Japan | 260/396 R |
| 928459 | 6/1963 | United Kingdom | 260/396 R |

*Primary Examiner*—Vivian Garner
*Attorney, Agent, or Firm*—Oblon, Fisher, Spivak, McClelland & Maier

[57] ABSTRACT

In a process for separation of naphthoquinone and phthalic acid from an aqueous slurry prepared by contacting a reaction mixture gas formed by a catalytic vapor phase oxidation of naphthalene with an aqueous medium, the decomposition of naphthoquinone is prevented and phthalic acid is substantially separated by adding a base to the aqueous slurry so as to neutralize only sulfuric acid component and maleic acid component without substantially neutralizing phthalic acid component and heating the aqueous slurry to dissolve phthalic acid to form a slurry of naphthoquinone in an aqueous solution of phthalic acid and extracting naphthoquinone with a solvent while preventing a crystallization of phthalic acid.

A pH of the aqueous slurry is adjusted in a range of 1.2 to 2.5 before the heat dissolution of phthalic acid and the extraction of naphthoquinone.

An aqueous phase obtained after the extraction of naphthoquinone is cooled to crystallize phthalic acid and then the filtrate separating from the resulting slurry is used as an aqueous medium for contacting with the reaction mixture gas, optionally after adjusting pH in a range of 1.2 to 2.5.

9 Claims, 3 Drawing Figures

PROCESS FOR SEPARATION OF NAPHTHOQUINONE AND PHTHALIC ACID

BACKGROUND OF THE INVENTION

1. Field of the Invention

The present invention relates to a process for a separation of naphthoquinone and phthalic acid. More particularly, it relates to a process for separation for naphthoquinone and phthalic acid from a reaction mixture gas produced by a catalytic vapor phase oxidation of naphthalene by washing the reaction mixture gas with water and collecting naphthoquinone and phthalic acid with water as an aqueous slurry and extracting naphthoquinone from the aqueous slurry with an organic solvent.

2. Description of Prior Arts

It has been proposed to produce naphthoquinone by contacting a reaction mixture gas formed by a catalytic vapor phase oxidation of naphthalene with water to collect main products of naphthoquinone and phthalic anhydride as an aqueous slurry of naphthoquinone and phthalic acid and heating the aqueous slurry at 60 to 95° C. to dissolve phthalic acid and extracting with an organic solvent which can be separated from water and has different specific gravity and a boiling point of 80 to 145° C. and separating and concentrating and drying naphthoquinone (Japanese Unexamined Patent Publication No. 47937/1975).

When a crude naphthalene is used in an industrial operation the reaction mixture gas formed by the catalytic vapor phase oxidation contains naphthoquinone, phthalic anhydride, maleic anhydride and a small amount of sulfuric anhydride derived from an oxidation of sulfur-containing compounds of thionaphthene etc. which are included as impurities in naphthalene.

It has been also proposed to produce naphthoquinone by a catalytic vapor phase oxidation of naphthalene in the presence of sulfur or sulfur-containing compounds (Japanese Unexamined Patent Publication No. 35369/1974). The reaction mixture gas also includes sulfuric anhydride.

In the industrial operation by the former process, it is necessary to combine a process for recovering phthalic acid as the by-product. In the practical operation, the aqueous slurry of phthalic acid and naphthoquinone is heated to dissolve only phthalic acid, and naphthoquinone is extracted with a solvent and the aqueous phase is cooled to crystallize phthalic acid and the crystallized phthalic acid is separated by a filtration.

In this case, a large amount of phthalic acid remains in the filtrate. In order to recover phthalic acid in high efficiency, the filtrate is recycled whereby the by-products of sulfuric acid and maleic acid are accumulated and the operation is carried out under the condition of several % of sulfuric acid content and several % of maleic acid content.

When a crude naphthalene is used as a raw material in the processes for recovering naphthoquinone and phthalic acid as disclosed in Japanese Unexamined Patent Publication No. 47937/1975, a purity and a yield of the resulting naphthoquinone are lowered. Sometimes, the naphthoquinone having relatively low purity of about 93% is obtained.

SUMMARY OF THE INVENTION

It is an object of the present invention to provide a process for separation of naphthoquinone and phthalic acid while preventing a decomposition of naphthoquinone to maintain high purity and high yield.

The foregoing and other objects of the present invention have been attained by (1) forming a reaction mixture gas containing naphthoquinone, phthalic anhydride, maleic anhydride and sulfuric anhydride and/or sulfuric acid by a catalytic vapor phase oxidation of naphthalene and contacting it wih an aqueous medium to collect naphthoquinone and phthalic anhydride as an aqueous slurry of naphthoquinone and phthalic acid; (2) heating the resulting aqueous slurry at 60 to 100° C. preferably 70° to 95° C. to dissolve phthalic acid to form an aqueous slurry in which naphthoquinone is dispersed in an aqueous solution of phthalic acid; (3) extracting naphthoquinone with a solvent which is separable from water; crystallizing phthalic acid by cooling an aqueous solution of phthalic acid separated from naphthoquinone-solvent phase; separating the crystallized phthalic acid by a filtration or a centrifugal separation and recycling the filtrate as the aqueous medium for the collection with water; wherein sulfuric acid and maleic acid formed as the by-products in the catalytic vapor phase oxidation are neutralized for 1 to 2 equivalents of sulfuric acid and 1 equivalent of maleic acid with a base such as basic alkali metal compounds, ammonia or basic ammonium compound; and then, the aqueous slurry is heated to dissolve phthalic acid and then, naphthoquinone is extracted to separate from it.

The neutralization with the base is controlled to give a pH of 1.2 to 2.5 preferably 1.5 to 2.2.

In the neutralization of sulfuric acid and maleic acid in the aqueous slurry of naphthoquinone and phthalic acid, the aqueous phase separated by extracting naphthoquinone that is the aqueous solution of phthalic acid is cooled and the crystallized phthalic acid is separated and the filtrate is neutralized to adjust the pH to 1.5 to 2.5 and the pH adjusted filtrate is used as the aqueous medium for collecting the reaction mixture gas, in recycling.

DETAILED DESCRIPTION OF PREFERRED EMBODIMENTS

The inventors have studied degradation of naphthoquinone and have found that decomposition of naphthoquinone is vigorously caused at higher than 70° C. in an aqueous solution of a strong acid especially in the presence of sulfuric acid. When 1.4% of maleic acid and the specific amount of sulfuric acid are added to an aqueous slurry containing 2.4% of naphthoquinone and 6.5% of phthalic acid and the mixtures are respectively stirred at 80° C. (B curve) or at 90° C. (A curve) for 4 hours, the results shown in FIG. 1 are found. As it is clear from the results, the presence of sulfuric acid remarkably affects the decomposition of naphthoquinone. When sulfuric acid is not added, the decomposition of naphthoquinone is not substantially caused even though maleic acid and phthalic acid are present. Then, sodium hydroxide is added to neutralize sulfuric acid component to adjust the pH of the aqueous solution from 1.0 to 2.1 (FIG. 1 point C), and then, the mixture is stirred at 80° C. or 90° C., it is found that the decomposition of naphthoquinone is substantially prevented.

When the aqueous slurry of naphthoquinone and phthalic acid is heated to dissolve phthalic acid and naphthoquinone is extracted by contacting with an organic solvent, the heat-treatment is usually carried out at 60° to 100° C. preferably 70° to 95° C.

When the reaction mixture gas formed by the catalytic vapor phase oxidation of naphthalene (air is usually used) is contacted with water to collect naphthoquinone and phthalic anhydride, the temperature of the reaction mixture gas is in a range of 180° to 250° C. whereby there is possibility to locally raise the temperature of the aqueous slurry.

As shown in FIG. 2; A curve, when sulfuric acid is present in the aqueous slurry of naphthoquinone and phthalic acid, and the aqueous slurry is heated at higher than 80° C., naphthoquinone is vigorously decomposed. Accordingly, is it clear that when sulfuric acid is present in the aqueous slurry of naphthoquinone in the step of collecting the reaction mixture gas formed by the catalytic vapor phase oxidation of a crude naphthalene with water, the step of dissolving phthalic acid and the step of extracting naphthoquinone, the decomposition of naphthoquinone is remarkably accelerated. The inventors have studied the method of preventing the decomposition of naphthoquinone and have found that the decomposition of naphthoquinone could be prevented by adjusting the pH of the aqueous slurry of naphthoquinone and phthalic acid to 1.2 to 2.5 by neutralizing 1 to 2 equivalents of sulfuric acid and 1 equivalent of maleic acid with a base such as an aqueous solution of sodium hydroxide.

It has been known to recover naphthoquinone by adding a base to dissolve phthalic acid as phthalate in the separation of naphthoquinone and phthalic acid from an aqueous slurry of naphthoquinone and phthalic acid prepared by collecting the reaction mixture gas formed by the catalytic vapor phase oxidation of naphthalene with water (Austria Pat. No. 242,124 and Japanese Unexamined Patent Publication No. 132042/1974). In both cases, phthalic acid in the aqueous slurry is converted to phthalate to dissolve it so as to separate naphthoquinone from phthalic acid at relatively low temperature. In order to recover phthalic acid in high efficiency, it is necessary to add a mineral acid such as sulfuric acid to crystallize phthalic acid. These processes are quite different from the process of the present invention.

In the process of the present invention phthalic acid is dissolved in the aqueous slurry at higher than 60° C. and naphthoquinone is extracted. In order to prevent the decomposition of naphthoquinone at higher than 60° C. the by-products of sulfuric acid and maleic acid which accelerate the decomposition of naphthoquinone are neutralized with a base. For the purpose, it is enough to neutralize 1 to 2 equivalents of sulfuric acid and 1 equivalent of maleic acid without neutralizing phthalic acid. Since phthalic acid is present in the aqueous phase in an acid form, phthalic acid can be easily separated as precipitate by cooling the aqueous phase after extracting naphthoquinone.

In the conventional process of Austria Pat. No. 242,124, a mixture of naphthoquinone and phthalic anhydride is heated with water at 80° C. to a boiling point to convert phthalic anhydride to phthalic acid and the mixture is cooled to 5° to 20° C. and neutralized with ammonia to pH 5 to 6 and naphthoquinone is separated from the aqueous solution of phthalic acid by a filtration.

In the conventional process of Japanese Unexamined Patent Publication No. 132042/1974, an aqueous slurry of naphthoquinone and phthalic acid is neutralized with a base to a pH of 2 to 5 preferably 3 to 4 lower than 60° C. to solubilize the acidic salt of phthalic acid and naphthoquinone is separated. In the example, pH of 4 for the acidic salt of phthalic acid is employed.

The disadvantages of these processes are to require a large amount of a base for producing the acid salt and to require a large amount of a mineral acid for acidifying the acidic salt to obtain phthalic acid because a content of phthalic anhydride is more than naphthoquinone. Moreover, a large amount of a mineral acid salt is included in the filtrate after separating phthalic acid and so the filtrate can not be reused in the system. When the filtrate is discharged as a waste, loss of dissolved phthalic acid is considered and the cost for preventing the environmental pollution is high.

On the contrary, in accordance with the process of the present invention, phthalic acid component is not substantially neutralized and an amount of a base can be quite small to neutralize only sulfuric acid and maleic acid which accelerate the decomposition of naphthoquinone.

Phthalic acid is dissolved by heating the aqueous slurry and naphthoquinone is extracted. The purpose of the neutralization, the method of the separating steps and the temperatures in the steps are different from the conventional processes, and an amount of a base is quite small and the filtrate after separating crystallized phthalic acid can be recycled to the step of collecting the reaction mixture gas to attain a closed system.

In the process of the present invention, air is usually used as an oxygen-containing gas in the catalytic vapor phase oxidation of naphthalene.

Suitable bases used in the process of the present invention include basic alkali metal compounds, ammonia and basic ammonium compounds such as alkali metal oxides, e.g. sodium oxide and potassium oxide; alkali metal hydroxides, e.g. sodium hydroxide and potassium hydroxide; alkali metal carbonates, e.g. sodium carbonate and potassium carbonate; alkali metal bicarbonates, e.g. sodium bicarbonate and potassium bicarbonate; alkali metal salts of organic acids, e.g. sodium phthalate and potassium maleate; ammonia water, ammonia, ammonia carbonate; weak acid salts e.g., ammonium salts of organic acids, and organic bases such as triethyl amine.

The base can be used in suitable form such as aqueous solution and powder. It is preferable to use the base in a form of aqueous solution. The amount of the base is enough to neutralize 1 to 2 equivalents of sulfuric acid ($\frac{1}{2}$–1 mole) and 1 equivalent of maleic acid ($\frac{1}{2}$ mole). It is possible to add the base so as to neutralize a small portion of phthalic acid, though it is disadvantageous because of excess of the base is used and the amount of phthalic acid recycled is increased.

The amounts of the base are studied by pH range to obtain the results shown in FIG. 3 wherein the relation of decomposition percent of naphthoquinone and pH of the aqueous slurries of naphthoquinone containing sulfuric acid, phthalic acid and maleic acid.

The test solution (1.5% of phthalic acid; 1.4% of maleic acid and 1.2% of sulfuric acid) is a mother liquor prepared by separating phthalic acid formed by cooling a hot aqueous solution of phthalic acid separated from naphthoquinone by the extraction. An aqueous solution of sodium hydroxide is added to the mother liquor to adjust the pH to 1.0, 1.2, 1.5, 1.9 and 2.1 and then, 2.4% of naphthoquinone and 5.0% of phthalic acid are added and the mixtures are respectively stirred at 80° C. for 4 hours.

As the results, it is found that the decomposition of naphthoquinone can be substantially prevented by the addition of sodium hydroxide to give a pH of 1.2 to 2.5 which corresponds to neutralize 1 equivalent of sulfuric acid and ½ equivalent of maleic acid. Accordingly, pH is selected from the range of 1.2 to 2.5 preferably 1.5 to 2.2.

In the industrial operation of the process, naphthoquinone is extracted and the aqueous solution is cooled to crystallize phthalic acid and it is separated by a filtration or a centrifugal separation and pH of the filtrate is adjusted in a range of 1.5 to 2.5 with an aqueous solution of sodium hydroxide and then, the pH adjusted filtrate is used as the aqueous medium in the step of collecting the reaction mixture gas. A content of sulfur in a crude naphthalene is usually less than 1%, accordingly, even though the pH adjusted filtrate is used for the step of collecting the reaction mixture gas, pH is not substantially changed in the step. Accordingly, the process of the present invention is suitable for a recycling process. In the process of the present invention, the temperature at the operation of the neutralization for sulfuric acid and/or maleic acid or the pH adjustment is usually in a range of 0° to 70° C. preferably 20° to 60° C.

The organic solvents used in the process of the present invention are not substantially miscible with water and have different specific gravity from that of the aqueous solution of phthalic acid and can be aromatic hydrocarbons, aliphatic hydrocarbons and derivatives thereof.

From the viewpoints of the temperature in the extraction step, the solubility of naphthoquinone, the separatability from the aqueous solution of phthalic acid and the desolvent property from the solvent solution of naphthoquinone, it is preferable to use hydrocarbons having a boiling point of 80° to 145° C. such as benzene, toluene and xylene. It is preferable to use xylene. An amount of the hydrocarbon solvent is usually more than 2 wt. times preferably 3 to 10 wt. times of naphthoquinone extracted.

An amount of water in the aqueous slurry of naphthoquinone and phthalic acid should be suitable to dissolve all of the phthalic acid by heating it at 60° to 100° C. preferably 70° to 95° C. or be suitable for separating it from the organic solvent solution of naphthoquinone in the extraction of naphthoquinone. It is usually 7 to 30 wt. times preferably 10 to 20 wt. times of phthalic acid dissolved in the aqueous slurry. The water can be fresh water or the aqueous medium used in the step of collecting the reaction mixture gas.

In the process of the present invention, the temperature for extracting naphthoquinone from the aqueous naphthoquinone slurry should be the temperature for dissolving all of the phthalic acid and is selected from a range of 60° to 100° C.

In usual, it is preferable to be higher concentration of phthalic acid so as to effectively attain the recovery of phthalic acid. Accordingly, the temperature is preferably higher. At higher than 100° C., the decomposition of naphthoquinone is severe as shown in FIG. 2. On the other hand, at lower than 60° C., the solubility of phthalic acid is too low. It is preferable to be in a range of 70° to 90° C. especially 80° to 90° C.

The solvent solution of naphthoquinone can be used in the following steps such as the Diels-Alder reaction for producing anthraquinone and also naphthoquinone can be separated by cooling it for crystallization or distilling off the solvent.

In accordance with the present invention, naphthoquinone and phthalic acid can be effectively obtained from the reaction gas mixture formed by the catalytic vapor phase oxidation of naphthalene while preventing the decomposition or degradation of naphthoquinone with a small amount of a base. The process is especially effective for the industrial process.

Figure 1:
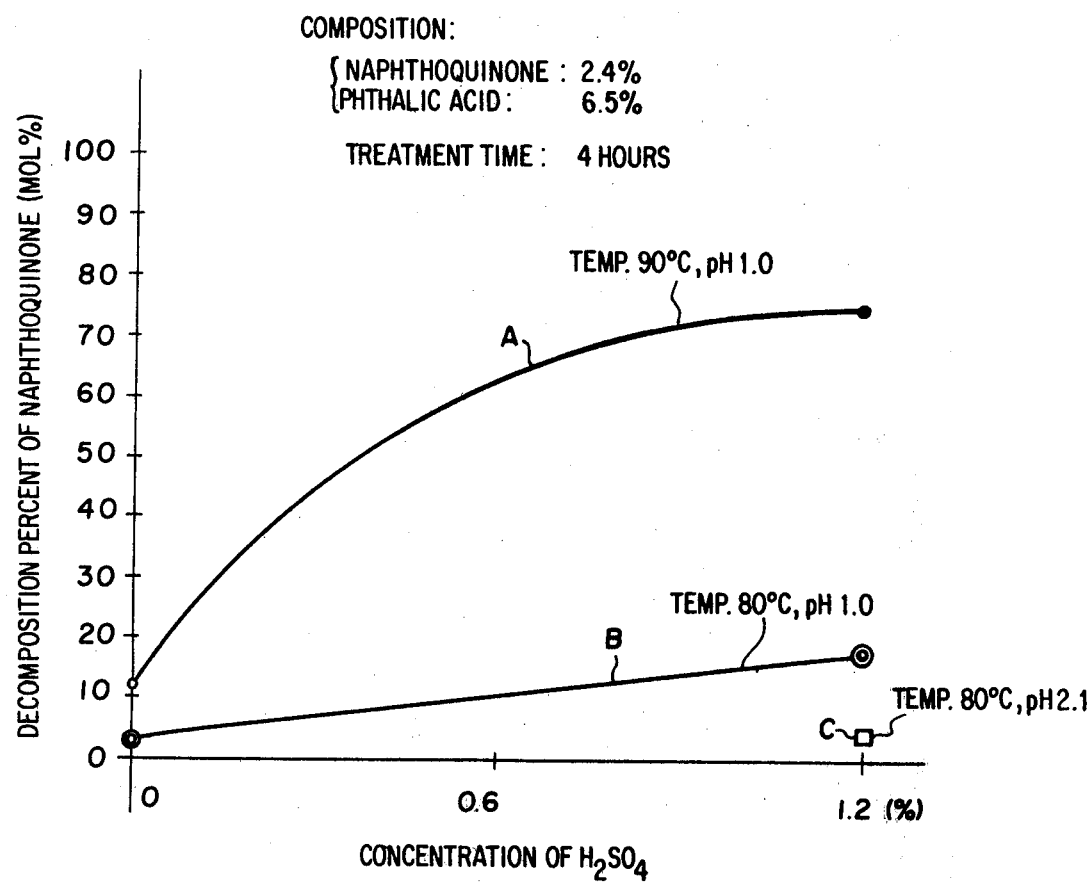
FIG. 1 shows the effect of a concentration of sulfuric acid for the decomposition of naphthoquinone in an aqueous solution of phthalic acid.
Figure 2:
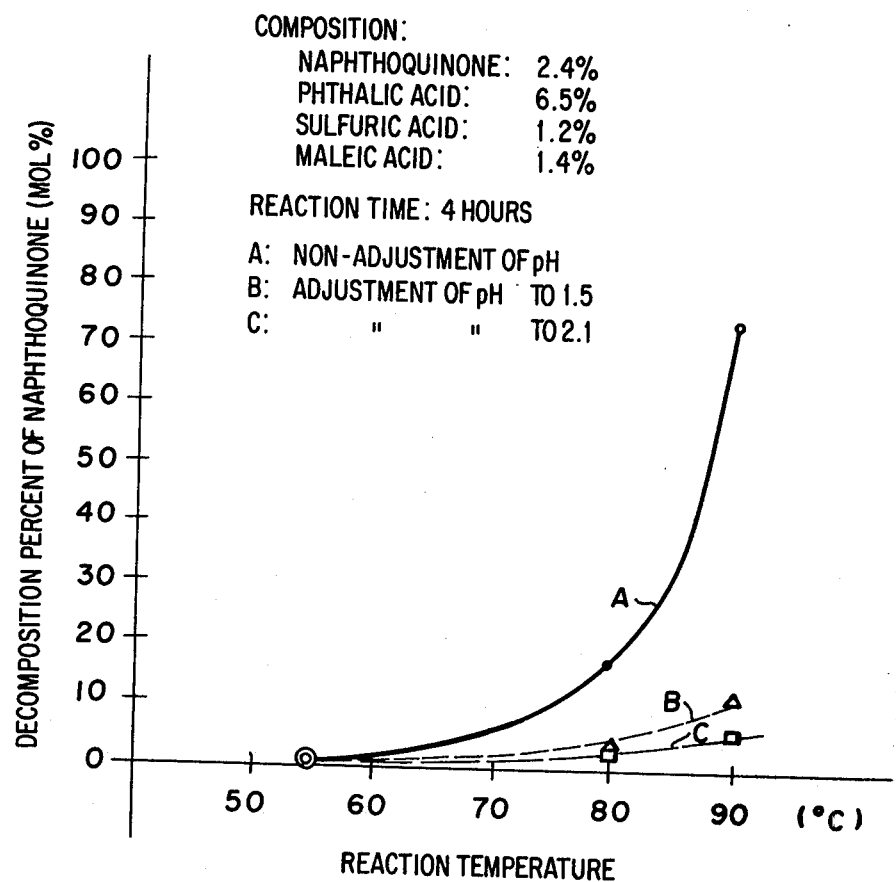
FIG. 2 shows the effect of a temperature for the decomposition of naphthoquinone in an aqueous solution of phthalic acid when pH is adjusted to 1.5 or 2.1.
Figure 3:
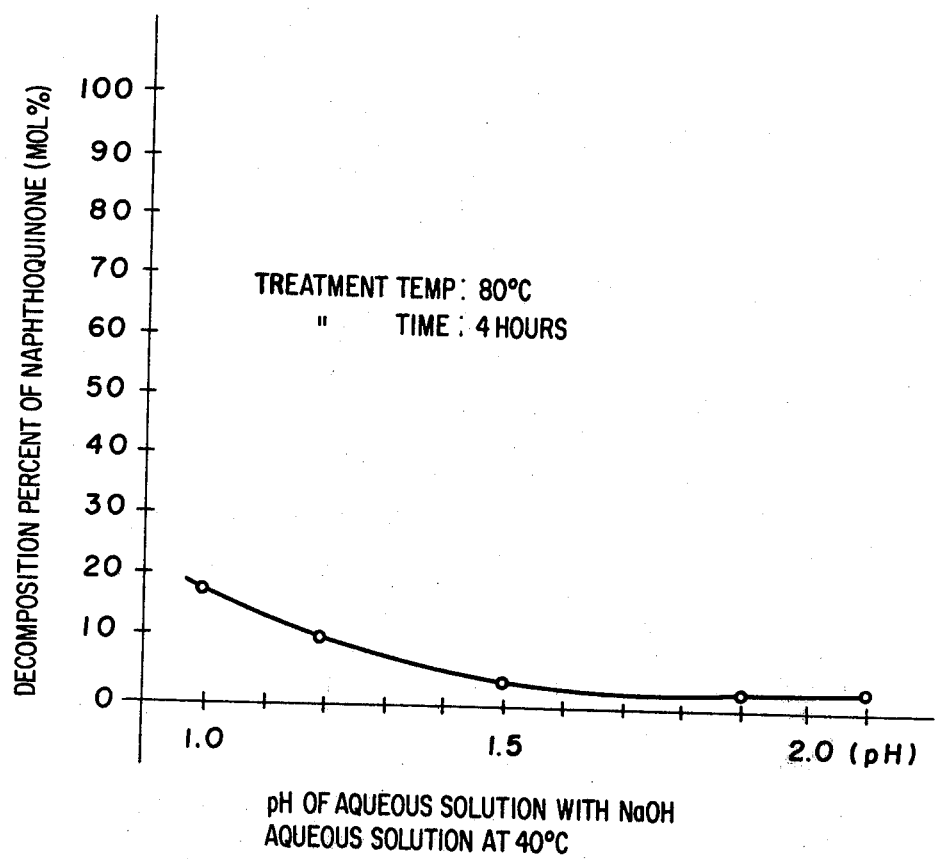
FIG. 3 shows the effect of pH for the decomposition of naphthoquinone in an aqueous solution of phthalic acid containing sulfuric acid and maleic acid.

The present invention will be illustrated by certain examples in detail. In the examples, the terms of "part" and "%" mean "part by weight" and "% by weight."

EXAMPLE 1

A reaction mixture gas formed by a catalytic vapor phase oxidation of naphthalene was contacted with water to obtain an aqueous slurry (pH 1.0) containing 1.4 wt. parts of naphthoquinone, 3.9 wt. parts of phthalic acid, 0.85 wt. part of maleic acid, 0.72 wt. part of sulfuric acid and 53.1 wt. parts of water. Then, 14.7 wt. parts of 4% aqueous solution of sodium hydroxide was added dropwise to the aqueous slurry at 20° C. under stirring and the mixture (pH 1.5) was heated to 85° C. to dissolve all of phthalic acid. Naphthoquinone was extracted from the slurry of naphthoquinone in a counter-current extraction with 5 wt. parts of xylene. The xylene phase was washed with hot water and concentrated and dried at 70° C. under a vacuum of 60 Torr to obtain 1.4 wt. parts of naphthoquinone having a purity of 96.5%.

REFERENCE 1

A reaction mixture gas formed by a catalytic vapor phase oxidation of naphthalene was contacted with water to obtain an aqueous slurry containing 1.4 wt. parts of naphthoquinone, 3.9 wt. parts of phthalic acid, 0.85 wt. part of maleic acid, 0.72 wt. part of sulfuric acid and 53.1 wt. parts of water. The aqueous slurry was heated to 85° C. to dissolve all of phthalic acid. Naphthoquinone was extracted from the slurry of naphthoquinone in a counter-current extraction with 5 wt. parts of xylene. The xylene phase was washed with hot water and concentrated and dried at 70° C. under a vacuum of 60 Torr to obtain 1.4 wt. parts of naphthoquinone having a purity of 93.2%.

EXAMPLE 2

An aqueous phase obtained by the below-mentioned process of extracting naphthoquinone was cooled and the resulting crystallized phthalic acid was separated to obtain a mother liquor containing 1.5 wt. parts of phthalic acid, 1.4 wt. parts of maleic acid, 1.2 wt. parts of sulfuric acid and 95.9 wt. parts of water. Then, 4% aqueous solution of sodium hydroxide was added to the mother liquor at 40° C. under stirring to adjust pH of 1.9.

A reaction mixture gas containing 5.0 wt. parts of phthalic anhydride and 2.4 wt. parts of naphthoquinone which was formed by a catalytic vapor phase oxidation, was cooled to 180° C. by a gas cooler and was introduced into the mother liquor (pH of 1.9) to obtain an aqueous slurry of naphthoquinone and phthalic acid. The slurry (pH 1.7) was heated to 85° C. to dissolve all of phthalic acid. Naphthoquinone was extracted from the slurry of naphthoquinone in a counter-current extraction with 8.0 wt. parts of xylene. The xylene phase was washed with hot water and concentrated and dried at 70° C. under a vacuum of 60 Torr to obtain 2.4 wt. parts of naphthoquinone having a purity of 96.7%.

On the other hand, the aqueous phase obtained by the xylene extraction was cooled at 40° C. and the crystallized phthalic acid was filtered. The resulting mother liquor was used as an aqueous medium for collecting the reaction mixture gas formed by a catalytic vapor phase oxidation, in the next operation.

EXAMPLE 3

15% ammonia water was added in the mother liquor of Example 2 at 40° C. under stirring to adjust pH of 1.5.

The reaction mixture gas formed by the catalytic vapor phase oxidation of Example 2 was introduced into the resulting mother liquor at the same temperature to obtain an aqueous slurry of naphthoquinone and phthalic acid.

In accordance with the process of Example 2, the aqueous slurry was treated to obtain 2.4 wt. parts of naphthoquinone having a purity of 96.0%.

REFERENCE 2

The reaction mixture gas formed by the catalytic vapor phase oxidation of Example 2 was introduced into the mother liquor or Example 2 (pH of 1.0) which was not modified to adjust pH, at the same temperature to obtain an aqueous slurry of naphthoquinone and phthalic acid.

In accordance with the process of Example 2, the aqueous slurry was treated to obtain 2.3 wt. parts of naphthoquinone having a purity of 93.8%.

What is claimed is:

1. A process for the separation of naphthoquinone and phthalic acid from a gaseous mixture containing naphthoquinone, phthalic anhydride, maleic anhydride and sulfuric anhydride or sulfuric acid obtained from the catalytic vapor phase oxidation of naphthalene comprising: contacting said mixture with an aqueous medium which collects naphthoquinone and phthalic anhydride as an aqueous slurry of napthoquinone and phthalic acid, adding a base to said aqueous slurry to adjust the pH from 1.2 to 2.5 in order to neutralize only sulfuric acid and maleic acid in said slurry without substantially neutralizing phthalic acid present therein;

heating the aqueous slurry to a temperature of 60° C. to 100° C. to dissolve said phthalic acid thereby forming a slurry of naphthoquinone in an aqueous solution of phthalic acid; and extracting naphthoquinone from said slurry with a solvent substantially immiscible with water while maintaining the temperature of the aqueous solution at a temperature sufficient to prevent crystallization of phthalic acid.

2. The process of claim 1, wherein said aqueous slurry is at a temperature of 70° C. to 95° C. when extracted.

3. The process of claim 1, wherein the base is added to the aqueous slurry to adjust the pH within the range of 1.5 to 2.2.

4. The process of claim 1, wherein the base is an oxide, hydroxide, carbonate or organic acid salt of an alkali metal or ammonia, ammonium hydroxide, ammonium carbonate or an ammonium salt of an organic acid.

5. The process of claim 1, wherein said solvent is an aromatic hydrocarbon or an aliphatic hydrocarbon.

6. The process of claim 1, wherein the amount of solvent employed is 3 to 10 times by weight the amount of naphthoquinone extracted.

7. The process of claim 1, wherein the amount of water (weight) in the aqueous phthalic acid-naphthoquinone slurry ranges from 7 to 30 times the amount (weight) of phthalic acid in the slurry.

8. The process of claim 1, wherein said aqueous phase obtained after extraction of naphthoquinone from said aqueous slurry is cooled to a temperature sufficient to crystallize phthalic acid, the crystallized phthalic acid is separated from the aqueous phase, and the aqueous phase obtained is recycled as the aqueous medium for contact with said gaseous mixture.

9. The process of claim 8, wherein said aqueous medium is adjusted to a pH within the range of 1.2 to 2.5 with base prior to contact with said gaseous mixture.

* * * * *

UNITED STATES PATENT AND TRADEMARK OFFICE
Certificate

Patent No. 4,202,828            Patented May 13, 1980

Ryo Matsuura, Tatsuyoshi Komatsu, Yukio Nomiyama, and Kenji Usui

Application having been made by Ryo Matsuura, Tatsuyoshi Komatsu, Yukio Nomiyama and Kenji Usui, the inventors named in the patent above identified, and Kawasaki Kasei Chemicals Ltd., the assignee, for the issuance of a certificate under the provisions of Title 35, Section 256, of the United States Code, deleting the name of Yukio Nomiyama as a joint inventor, and a showing and proof of facts satisfying the requirements of the said section having been submitted, it is this 10th day of July, 1984, certified that the name of the said Yukio Nomiyama is hereby deleted from the said patent as a joint inventor with the said Ryo Matsuura, Tatsuyoshi Komatsu, and Kenji Usui.

Fred W. Sherling,
*Associate Solicitor.*